United States Patent
Goos et al.

(10) Patent No.: US 10,786,390 B2
(45) Date of Patent: Sep. 29, 2020

(54) APPARATUS FOR EYE LASER SURGERY AND METHOD FOR PERFORMING A TRANSEPITHELIAL PHOTOREFRACTIVE KERATECTOMY

(71) Applicant: Wavelight GmbH, Erlangen (DE)

(72) Inventors: Evi Goos, Erlangen (DE); Christian Wuellner, Erlangen (DE)

(73) Assignee: Alcon Inc. (CH)

( * ) Notice: Subject to any disclaimer, the term of this patent is extended or adjusted under 35 U.S.C. 154(b) by 524 days.

(21) Appl. No.: 15/099,421

(22) Filed: Apr. 14, 2016

(65) Prior Publication Data

US 2016/0374858 A1 Dec. 29, 2016

(30) Foreign Application Priority Data

Jun. 24, 2015 (DE) .................. 10 2015 008 127

(51) Int. Cl.
*A61F 9/008* (2006.01)
*A61B 34/00* (2016.01)

(52) U.S. Cl.
CPC .......... *A61F 9/00814* (2013.01); *A61B 34/25* (2016.02); *A61F 9/00804* (2013.01); *A61F 2009/00853* (2013.01); *A61F 2009/00872* (2013.01)

(58) Field of Classification Search
CPC ........ A61F 9/00804; A61F 2009/00872; A61F 9/00814; A61F 2009/00853; A61B 34/25
See application file for complete search history.

(56) References Cited

U.S. PATENT DOCUMENTS

| | | | |
|---|---|---|---|
| 4,590,598 A | 5/1986 | O'Harra | |
| RE37,504 E * | 1/2002 | Lin | A61F 9/008 606/5 |
| 6,364,873 B1 * | 4/2002 | McMillen | A61F 9/008 235/382 |
| 7,736,382 B2 * | 6/2010 | Webb | A61N 5/0601 606/10 |
| 9,744,077 B2 * | 8/2017 | Zickler | A61F 2/16 |
| 2007/0161972 A1 | 7/2007 | Felberg et al. | |
| 2007/0213697 A1 | 9/2007 | Holliday | |

(Continued)

FOREIGN PATENT DOCUMENTS

| | | |
|---|---|---|
| CN | 102470048 A | 5/2012 |
| CN | 104287888 B | 5/2012 |

(Continued)

*Primary Examiner* — Christopher Koharski
*Assistant Examiner* — Amanda L Steinberg

(57) ABSTRACT

An apparatus for laser eye surgery comprises a laser module, which is equipped to emit pulsed, focused laser radiation of a variable pulse repetition rate, and a processor-based control unit, which is equipped to receive at least one user input pertaining to a selection of one of several predefined pulse repetition rates over a user input and to control the laser module in accordance with the selected pulse repetition rate. In certain specific embodiments, the user interface enables input of two user entries, each of which relates to a selection of one of several predefined pulse repetition rates. The control unit controls the laser module for a first phase of a laser treatment in accordance with one input, and for a second phase of the laser treatment, it controls the laser module in accordance with the other input.

8 Claims, 1 Drawing Sheet

(56) References Cited

U.S. PATENT DOCUMENTS

| | | | |
|---|---|---|---|
| 2007/0282313 A1 | 12/2007 | Huang et al. | |
| 2009/0247997 A1* | 10/2009 | Watanabe | A61F 9/008 606/4 |
| 2012/0165801 A1 | 6/2012 | Bragagna et al. | |
| 2014/0114297 A1* | 4/2014 | Woodley | A61F 9/008 606/6 |

FOREIGN PATENT DOCUMENTS

| | | | | |
|---|---|---|---|---|
| EP | 0164751 A3 | | 4/1988 | |
| EP | 0609978 A1 | | 8/1994 | |
| EP | 1549237 B1 | * | 11/2013 | A61F 9/008 |
| WO | 95/27534 A1 | | 10/1995 | |
| WO | 01/35881 A1 | | 5/2001 | |
| WO | 03101326 A1 | | 12/2003 | |
| WO | 2013/013690 A1 | | 1/2013 | |

\* cited by examiner

APPARATUS FOR EYE LASER SURGERY AND METHOD FOR PERFORMING A TRANSEPITHELIAL PHOTOREFRACTIVE KERATECTOMY

CROSS REFERENCE TO RELATED APPLICATIONS

This application claims priority to German Patent Application Serial Number 102015008127.6, filed 24 Jun. 2015, titled "APPARATUS FOR EYE LASER SURGERY AND METHOD FOR PERFORMING A TRANSEPITHELIAL PHOTOREFRACTIVE KERATECTOMY," which is hereby incorporated by reference in its entirety.

FIELD OF INVENTION

The present disclosure relates in general to an apparatus and a method for treating eye tissue by means of pulsed laser radiation. The present disclosure in particular relates to the removal of eye tissue by means of pulsed laser radiation.

BACKGROUND

There are various known surgical methods in refractive eye surgery using pulsed laser radiation for ablation, i.e., removal, of corneal eye tissue. The term "ablation" has frequently been used in the technical world for this removal of tissue. In these surgical methods, an ablation profile, indicating where in the eye there is too much corneal tissue that must be removed, is prepared individually for each patient. The ablation profile is selected so that, after the surgery, the result is a shape of the anterior surface of the eye which eliminates or at least greatly reduces the pre-existing abnormality of vision of the eye (e.g., myopia, hyperopia, astigmatism).

Traditional surgical methods in which ablation of corneal eye tissue is performed by means of pulsed laser radiation include, for example, LASIK (laser in-situ keratomileusis) and transepithelial PRK (photorefractive keratectomy). In LASIK, a cover flap is first cut in the region of the anterior corneal surface, while the flap is still attached to the surrounding corneal tissue in a hinge area. This cover disk (usually referred to as a "flap" in the technical world) is folded to the side. Then, depending on the ablation profile determined specifically for each patient, laser ablation is performed on the stromal tissue of the cornea thereby exposed. After the ablation is concluded, the flap is folded back and the surgical wound is closed. In transepithelial PRK, however, material is ablated through the corneal epithelium. The epithelium is removed completely in the ablation region. Since epithelium can regenerate, transepithelial PRK also does not leave a wound that is permanently open.

BRIEF SUMMARY

Traditional laser systems, which are suitable for tissue ablation within the context of treatment of a human eye, have a predetermined pulse repetition rate (i.e., frequency of laser radiation pulses emitted by the laser system), which cannot be influenced by the treating personnel (physician, assistant). A physician working with such a laser system therefore has no leeway for using a different pulse repetition rate, depending on the patient or the type of treatment. The physician must use the same pulse repetition rate in treating all patients. A fixed pulse repetition rate may raise objections with the physician or the patient in particular if the pulse repetition rate is comparatively high, for example, more than 1000 Hz. Because of the faster sequence of radiation pulses, the local heating that occurs in the eye may be greater than that with a lower pulse repetition rate. Fears in conjunction with such local tissue heating may cause the operators of eye clinics or medical practices, where laser-assisted eye surgery is offered, to decide against a more modern laser system that works with a higher pulse repetition rate instead of relying on an older system that operates with a lower pulse repetition rate.

One object of embodiments of the invention is to provide an apparatus for ablative laser treatment of an eye that can be used in a variety of ways.

According to specific embodiments of the invention, an apparatus for laser eye surgery is provided, comprising a laser module, which is equipped to emit pulsed focused laser radiation of a variable pulse repetition rate; and a processor-based control unit, which is equipped to receive at least one user input pertaining to a selection of one or more predefined pulse repetition rates over a user interface and to control the laser module in accordance with the at least one selected pulse repetition rate. Such an apparatus allows the physician to select freely among various pulse repetition rates for a pending treatment. The user interface is designed to allow the physician a corresponding input of a selected pulse repetition rate. For example, the user interface may comprise a graphical user interface that is displayed on a screen. The graphical user interface may comprise, for example, at least one drop-down menu, which presents at least two predefined pulse repetition rates for selection.

Criteria for the selection to be made by the physician may include, for example, individual preferences of the physician as well as the duration of treatment. The higher the selected pulse repetition rate, the shorter is the treatment time. In a case in which a comparatively small tissue volume is to be removed on the whole and the number of required radiation pulses is comparatively low accordingly, the physician can select, for example, a lower pulse repetition rate than in a case when a larger tissue volume is to be removed on the whole and more radiation pulses are needed accordingly. Nevertheless, a treatment time that is acceptable for the patient can be determined in both cases.

For physicians who have fundamental objections to higher pulse repetition rates, an apparatus according to the invention is suitable. Physicians can now use a modern laser system while at the same time selecting a comparatively low pulse repetition rate if they have concerns about possible local thermal overheating of the eye tissue at a high pulse repetition rate.

Instead of a selection option displayed on a screen connected to a computer, for example, it is conceivable to provide a knob or some other electromechanical operating element by means of which the physician can enter his selection of the desired pulse repetition rate.

According to specific embodiments, the control unit may be configured to receive at least one user input in allocation to patient-specific data and to store the selected pulse repetition rate in a memory medium, where it is assigned to the patient-specific data. The storage may serve the purpose of archiving, so that it will be possible, at a time in the future, to reconstruct which pulse repetition rate was selected for a certain treatment by the physician. The control unit can compile the corresponding information in a data record, for example, which it then stores permanently in a suitable memory medium. The patient-specific data may comprise, for example, information about the respective patient (for example, a patient identification number and/or a patient name) and/or diagnostic data ascertained for the respective patient and/or treatment data (e.g., an ablation profile or a shot pattern), which specify the details of a laser treatment planned for the respective patient.

In specific embodiments of the invention, it is provided that the control unit is configured to receive two user inputs each pertaining to a selection of one of several predefined pulse repetition rates in assignment to a specific patient and control the delivery of a first part of a pulse emission sequence defined for the specific patient in accordance with the selected pulse repetition rate of one of the two user inputs and to control the delivery of a second part of the pulse emission sequence in accordance with the selected pulse repetition rate of the other one of the two user inputs. In this way, the physician can select a suitable pulse repetition rate individually for each one of different phases of a treatment (wherein each phase corresponds to a portion of the pulse emission sequence). In the example of transepithelial photorefractive keratectomy, the control unit may be equipped to perform a phase of epithelial tissue ablation using the selected pulse repetition rate of one of the two user inputs and to perform a phase of stromal tissue ablation using the selected pulse repetition rate of the other one of the two user inputs. For example, the physician can decide to ablate the epithelium at a higher pulse repetition rate and to perform the actual refractive correction, i.e., the ablation of stromal tissue, at a lower pulse repetition rate. In specific embodiments of the invention, the control unit is configured to create an uninterrupted delivery of the pulse emission sequence. If different pulse repetition rates have been selected by the physician for different parts of the pulse emission sequence, then in such embodiments, the control unit switches instantaneously, i.e., without a delay, between the selected pulse repetition rates.

In embodiments of the invention, the control unit is configured to receive optionally the same selected pulse repetition rate or different selected pulse repetition rates for the two user inputs. In these embodiments, the control unit thus enables the physician to either select different pulse repetition rates for different parts of a pulse emission sequence (corresponding to different phases of a treatment) or to select the same pulse repetition rate as needed for all parts of the pulse emission sequence.

The emitted laser radiation in embodiments of the invention has radiation properties, which cause ablation of eye tissue on irradiation of an eye with the laser radiation. For example, the emitted laser radiation has radiation wavelength of less than 300 nm to prevent transmission of laser radiation into the eye as much as possible. The predefined pulse repetition rates are in a range below 3 kHz or below 2 kHz or below 1500 Hz, for example. In embodiments of the invention, the predefined pulse repetition rates include at least one of the following pulse repetition rates: approx. 210 Hz, approx. 262.5 Hz, approx. 525 Hz and approx. 1050 Hz.

According to another aspect, the present disclosure provides a method for performing transepithelial photorefractive keratectomy, comprising: receiving a first and a second user input via a user interface, wherein each of the first and second user inputs relates to a selection of one of several predefined pulse repetition rates; controlling the delivery of radiation pulses of a laser module during a phase of epithelial tissue ablation using the selected pulse repetition rate of the first user input; and controlling the delivery of radiation pulses of the laser module during a phase of stromal tissue ablation using the selected pulse repetition rate of the second user input.

BRIEF DESCRIPTION OF THE DRAWINGS

The invention is explained in greater detail below on the basis of the accompanying drawings, in which.

DETAILED DESCRIPTION OF EMBODIMENTS

Figure 1:
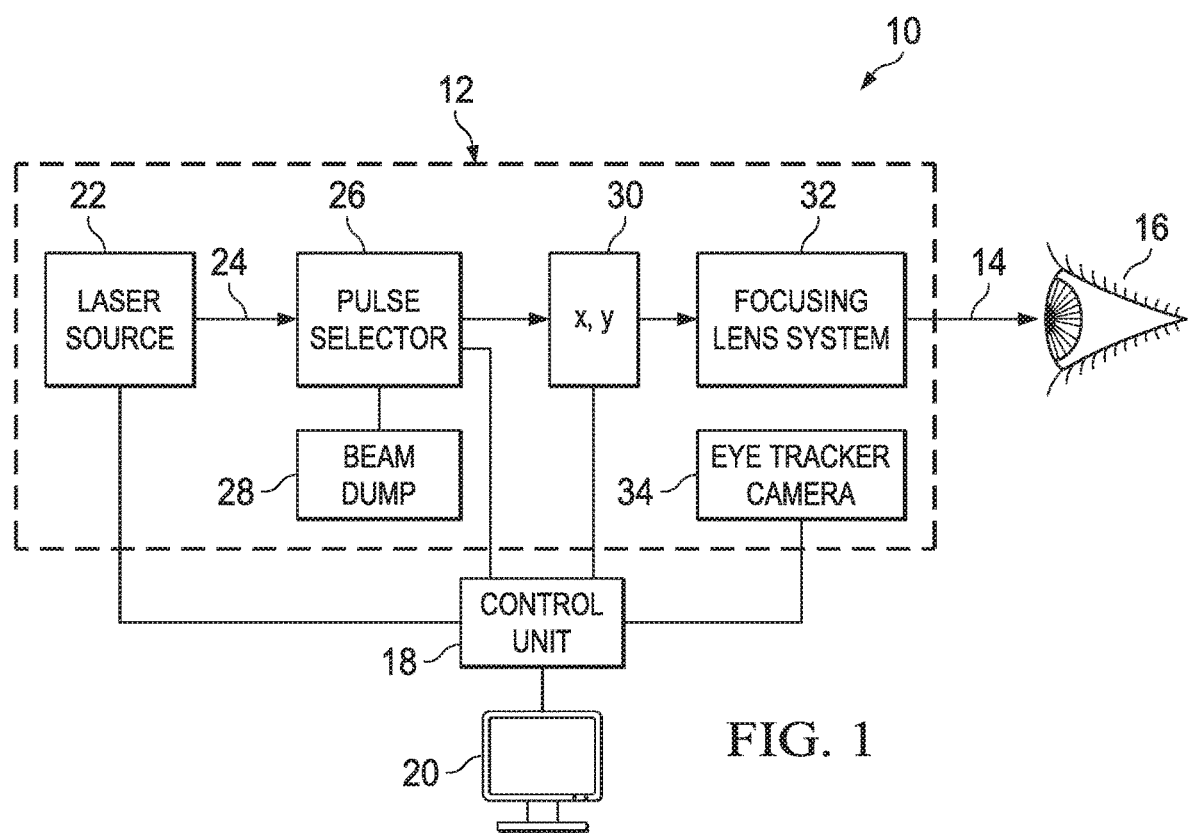
FIG. 1 shows, in a schematic block diagram, the components of the laser system for ablative laser treatment of a human eye.

Reference is made first to FIG. 1. The laser system shown there is labeled as 10 in general. It comprises a laser module 12 (outlined with a dotted line) consisting of a plurality of individual components capable of emitting a pulsed focused laser beam 14 in the direction of an eye 16 to be treated. The laser system 10 also has a program-controlled control unit 18, which is shown in the schematic diagram in FIG. 1 as a single block, but in certain embodiments, its functions may be distributed over a plurality of decentralized control subunits. The control unit 18 is connected to a monitor 20 on which the control unit 18 can display a graphical user interface by means of which a physician or a physician's assistant can enter user commands for controlling the laser module 12. The monitor 20 may be designed as a touch-sensitive display screen (touch screen), for example, so that the user can enter his commands by touching the surface of the monitor. Alternatively or additionally, the control unit 18 may be designed to display on the graphical user interface a cursor, which can be moved by a mouse or some other suitable cursor movement device over the graphical user interface to make inputs in that way.

By means of the graphical user interface, the user can select the pulse repetition rate of the laser beam 14 emitted by the laser module 12. For example, a plurality of preset pulse repetition rates may be offered to the user on the graphical user interface so that the user can select among them. Each of the predefined pulse repetition rates corresponds to an integral divisor of a largest available repetition rate, for example. To give a numerical example, the predefined pulse repetition rates may include a repetition rate of approx. 262.5 Hz as the smallest repetition rate and additional repetition rates of approx. 525 Hz and 1050 Hz as integral multiples of the smallest repetition rate. In this example, the repetition rate of 1050 Hz is the largest available repetition rate, and the repetition rates of 525 Hz and 262.5 Hz can be obtained by halving and quartering, respectively, the 1050 Hz repetition rate.

The laser module 12 comprises a laser source 22, which is designed, for example, as an excimer laser and generates pulsed laser radiation 24 with a radiation wavelength of less than approx. 300 nm. With such a radiation wavelength, transmission into deeper tissue regions of the eye 16 is avoided and instead an interaction of the radiation with the eye tissue in the region of the surface of the irradiated tissue region is achieved, wherein tissue ablation is achieved due to this interaction.

The laser radiation 24 generated by the laser source 22 has a given pulse repetition rate which is at least as great as the highest pulse repetition rate that can be selected by the user for the laser beam 14 emitted. In certain embodiments, the pulse repetition rate of the laser radiation 24 generated by the laser source 22 is equal to the highest pulse repetition that can be selected for the emitted laser beam 14. By means of a pulse selector 26 the pulses of the laser radiation 24 which should run further on the beam path in the direction of the eye 16 are selected. Any radiation pulses that are not selected and that should be allowed through in the direction of the eye 16 are deflected by the pulse selector 26 into a beam dump 28. The pulse selector 26 may comprise, for example, a mirror, which is positioned movably and can be controlled by the control unit 18 with regard to its mirror position, namely such that the mirror in a first mirror position deflects pulses of the laser radiation 24 in the direction of the eye 16 (or allows them to pass through) and in the second mirror position the mirror causes a defection of incoming pulses of the laser radiation 24 in the direction of the beam dump 28. The control unit 18 controls the mirror position of the selector mirror of the pulse selector 26 in accordance with the pulse repetition rate(s) selected by the user on the graphical user interface.

The laser module 12 also comprises an x, y scanner 30 as well as a focusing lens system 32, from which the focused laser beam emerges. The x, y scanner 30 allows a displacement of a focal point of the laser beam 14 in an x, y plane orthogonal to the beam propagation direction, where the letters x and y stand for a right-angled pair of axes (x axis and y axis) spanning this plane. The x, y scanner 30 is controlled by the control unit 18 in accordance with a control program, which represents an ablation profile that is defined for a specific patient in the form of a shot pattern, for example. Such a shot pattern defines x, y coordinates for a plurality of shot positions at which a radiation pulse is to be directed. Assuming a given tissue volume that can be ablated per radiation pulse, the amount of tissue ablated in this position can be determined on the basis of the number of radiation pulses aimed at a certain x, y shot position. Conversely, assuming given ablation volume per radiation pulse from an ablation profile that has been determined diagnostically, indicating in which location in the eye 16 how much tissue is to be ablated, in which location, the number of radiation pulses (i.e., shots) that must be directed at the respective location can be ascertained. The x, y scanner 30 may comprise a pair of galvanometrically driven scanner mirrors, for example, which are arranged so that they can be tilted about mutually perpendicular tilt axes.

The laser system 10 includes an eye tracker function to compensate for movements of the eye 16 while being bombarded with the pulses of the laser beam 14. The laser module 12 here includes an eye tracker camera 34, which supplies its camera images in the form of corresponding image data to the control unit 18, which analyzes the camera images and detects movements of the eye 16 on the basis of the sequence of camera images. Based on recognized movements of the eye 16, the control unit 18 adapts the x, y shot positions for the radiation pulses of the laser beam 14 accordingly.

For the image analysis of the camera images supplied by the eye tracker camera 34, the control unit 18 determines the position and/or orientation of at least one reference feature of the eye 16 in a coordinate system used by the eye tracker function. One example of a reference feature is the center of the pupil of the eye 16. Another reference feature of the eye 16 is, for example, an iris structure or a blood vessel that is visible in the sclera of the eye 16. On the basis of tracking of the x, y position of the center of the pupil and optionally the position of an iris or sclera structure in an x, y plane, the eye tracker function can detect, for example, translational and rotational movements of the eye 16.

The eye tracker function of the laser system 10 supplies a recognized eye movement in a regular interval pertaining to data to a control function of the control unit 18, which is responsible for control of the x, y scanner 30. This interval corresponds to at least the highest pulse repetition rate that can be defined by the user on the basis of the graphical user interface for the laser beam 14 emitted. If the greatest possible pulse repetition rate that can be selected by the user is 1050 Hz, for example, then the eye tracker function supplies corresponding movement data about recognized movements of the eye 16 at a rate equal to or greater than 1050 Hz.

Regardless of the repetition rate of the laser beam 14 selected for a specific patient, i.e., for a certain laser treatment, the eye tracker function of the laser system 10 always supplies movement data pertaining to recognized movements of the eye 16 at a rate that is always the same. It is possible in this way to access a traditional eye tracker for the eye tracker function. Depending on the selected pulse repetition rate of the laser beam 14, the control function of the control unit 18 which is responsible for controlling the x, y scanner 30 uses only the movement data corresponding to the rhythm of the selected pulse repetition rate. If the selected pulse repetition rate is lower than the rate at which the eye tracker function determines movement data for the eye 16, then the control unit 18 disregards some of these movement data accordingly in control of the x, y scanner 30.

Figure 2:
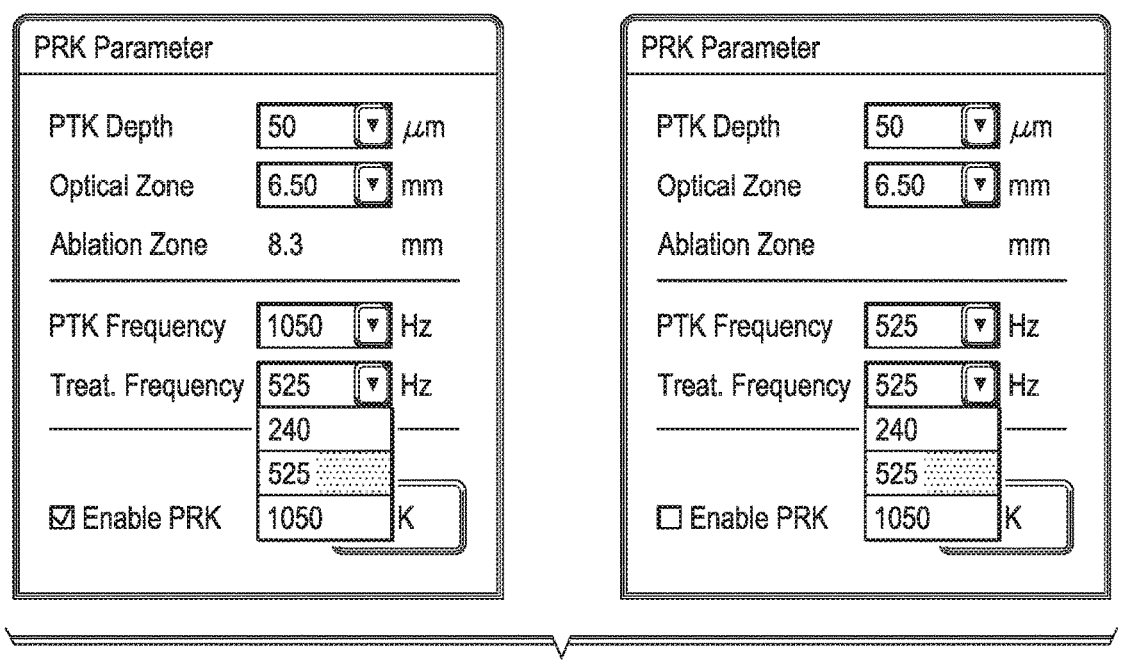
FIG. 2 shows two examples of a menu window as it may appear on a computer monitor as part of a graphical user interface of the laser system for selecting a pulse repetition rate.

In certain embodiments the graphical user interface displayed on the monitor 20 allows the user to select not only a single pulse repetition rate for an imminent laser treatment of a patient, but also to select a pulse repetition rate for each one of the different phases of the laser treatment. In this regard, reference is now also made to FIG. 2, which shows a menu window in its left half, which can be displayed as part of the graphical user interface, and allows the user to select a pulse repetition rate of the laser beam 14 for a phase of epithelial tissue ablation for a transepithelial keratectomy and also to select a pulse repetition rate for a subsequent phase of stromal tissue ablation. The "PTK Frequency" parameter in the menu window denotes the pulse repetition rate for epithelial tissue ablation, while the "Treat. Frequency" parameter denotes the pulse repetition rate for the stromal tissue ablation. For both parameters, the menu window offers a drop-down menu which, allows the user to select one of a plurality of predetermined repetition rates. In the example of FIG. 2, the repetition rates 210 Hz, 525 Hz and 1050 Hz are available for both parameters. In the example shown here, the repetition rate of 1050 Hz is selected for the "PTK Frequency" parameter. The repetition rate 525 Hz is selected for the "Treat. Frequency" parameter in the example shown here. In this section, epithelial tissue ablation should thus take place at a higher repetition rate than the subsequent stromal tissue ablation. The epithelial tissue ablation extends to the entire thickness of the epithelium within the intended ablation zone. The menu window in the left part of FIG. 2 provides in the illustrated exemplary case a value of 50 μm for the epithelial thickness (this value is input in advance by a user based, e.g., on a preceding measurement of the epithelial thickness) m and a value of 6.50 mm for the diameter of the ablation zone. The epithelial tissue ablation is thus performed at a repetition rate of 1050 Hz over a thickness of 50 μm in a region with a diameter of 6.50 mm. As the process is continued the control unit 18 then switches to the repetition rate of 525 Hz, which is selected for the "Treat. Frequency" parameter, and the remainder of the transepithelial keratectomy is performed at this repetition rate, in particular that portion of the treatment associated with the stromal tissue ablation.

The right part of FIG. 2 shows the same menu window as in the left part but in the right part the function for the selection of a repetition rate for the "PTK Frequency" parameter has been deactivated. The user can optionally perform an activation and deactivation of the function for the selection of a repetition rate for the "PTK Frequency" parameter by using a switch area located in the lower left portion of the menu window and identified with the legend "Enable PRK." In deactivation of this function (as in the right part of FIG. 2), the user has available only one selection option for the repetition rate of the "Treat. Frequency" parameter. This option is suitable for treatment forms in which only stromal tissue ablation is necessary (for example, in a LASIK treatment) but not an epithelial tissue ablation.

It is self-evident that the menu window according to FIG. 2 is just an example and serves only the purpose of illustration. The graphical user interface can use any other forms of representation to allow the user to select a pulse repetition rate for the laser beam 14 emitted.

In the left part of FIG. 2, the selection of the pulse repetition rate 1050 Hz for the "PTK Frequency" parameter corresponds to a first user input in the sense of the invention while the selection of the pulse repetition rate 525 Hz for the "Treat. Frequency" parameter corresponds to a second user input in the sense of the invention.

The invention claimed is:

1. An apparatus for eye laser surgery, comprising:
   a laser assembly configured to emit pulsed focused laser radiation having a variable pulse repetition rate; and
   a processor based control unit configured to:
      receive at least two user inputs for an execution of a transepithelial photorefractive keratectomy, each user input related to a selection of one from a plurality of pre-defined pulse repetition rates through a user interface, a first selected pulse repetition rate for a phase of epithelial tissue removal, a second selected pulse repetition rate for a phase of stromal tissue removal, the first selected pulse repetition rate higher than the second selected pulse repetition rate, the user inputs associated with patient-specific data;
      control the laser assembly in accordance with the at least one selected pulse repetition rate by performing the phase of epithelial tissue removal using the first selected pulse repetition rate, and by performing the phase of stromal tissue removal using the second selected pulse repetition rate; and
      store the selected pulse repetition rates in a storage medium, where the rates are assigned to the patient-specific data.

2. The apparatus of claim 1, wherein the user interface includes a graphical user interface displayed on a display screen.

3. The apparatus of claim 2, wherein the graphical user interface includes at least one drop-down menu adapted to allow a selection from at least two pre-defined pulse repetition rates.

4. The apparatus of claim 1, wherein the control unit is configured to effect an uninterrupted emission of the pulse emission sequence.

5. The apparatus of claim 1, wherein the emitted laser radiation has radiation characteristics causing a removal of eye tissue upon irradiation of an eye with the laser radiation.

6. The apparatus of claim 1, wherein the emitted laser radiation has a radiation wavelength below 300 nm.

7. The apparatus of claim 1, wherein the pre-defined pulse repetition rates are in a range below 1500 Hz.

8. The apparatus of claim 1, wherein the pre-defined pulse repetition rates include at least one of the following pulse repetition rates: about 210 Hz, about 262.5 Hz, about 525 Hz and about 1050 Hz.

* * * * *